United States Patent
Takimoto et al.

(10) Patent No.: US 8,727,992 B2
(45) Date of Patent: May 20, 2014

(54) ULTRASONIC DOPPLER DIAGNOSTIC APPARATUS, AND METHOD OF CONTROLLING ULTRASONIC DOPPLER DIAGNOSTIC APPARATUS

(75) Inventors: Masao Takimoto, Otawara (JP);
Muneki Kataguchi, Nasushiobara (JP);
Akihiro Kakee, Nasushiobara (JP);
Tomohisa Imamura, Nasushiobara (JP);
Fumiyasu Sakaguchi, Otawara (JP);
Atsushi Sumi, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 1575 days.

(21) Appl. No.: 11/756,261

(22) Filed: May 31, 2007

(65) Prior Publication Data
US 2008/0009737 A1    Jan. 10, 2008

(30) Foreign Application Priority Data
Jun. 2, 2006   (JP) ................................. 2006-155065

(51) Int. Cl.
*A61B 8/00*    (2006.01)
(52) U.S. Cl.
USPC .......................................... 600/454; 600/441
(58) Field of Classification Search
USPC ........................................................ 600/454
See application file for complete search history.

(56) References Cited

U.S. PATENT DOCUMENTS

| 4,205,687 A * | 6/1980 | White et al. ................... 600/455 |
| 5,287,753 A * | 2/1994 | Routh et al. ............... 73/861.25 |
| 2004/0019278 A1 * | 1/2004 | Abend ........................... 600/454 |

FOREIGN PATENT DOCUMENTS

| JP | 4-176447 | 6/1992 |
| JP | 9-26336 | 1/1997 |
| JP | 2863624 | 12/1998 |
| JP | 11-290323 | 10/1999 |
| JP | 2000-229082 | 8/2000 |
| JP | 2004-313551 | 11/2004 |
| JP | 2005-185731 | * 7/2005 |

OTHER PUBLICATIONS

Japanese Office Action issued Aug. 9, 2011, in Patent Application No. 2006-155065 (with English-language translation).

* cited by examiner

*Primary Examiner* — Tse Chen
*Assistant Examiner* — Hien Nguyen
(74) *Attorney, Agent, or Firm* — Oblon, Spivak, McClelland, Maier & Neustadt, L.L.P.

(57) ABSTRACT

An ultrasonic Doppler diagnostic apparatus sends ultrasonic waves to a specimen, receives a reflection signal of the ultrasonic waves from the specimen to detect a Doppler signal, obtains blood flow information indicating a peak flow velocity of coronary blood flow, and displays the flow velocity information before and after the administration of a drug to the specimen on a display unit. Then, at least velocity ranges of the flow velocity information before and after the administration of the drug to the specimen are adjusted, and during an ultrasonic scan of the specimen, data on a plurality of acquired images having different velocity ranges are adjusted to the same velocity range. A system control unit displays the data on the plurality of images adjusted to the same velocity range on the display unit.

11 Claims, 15 Drawing Sheets

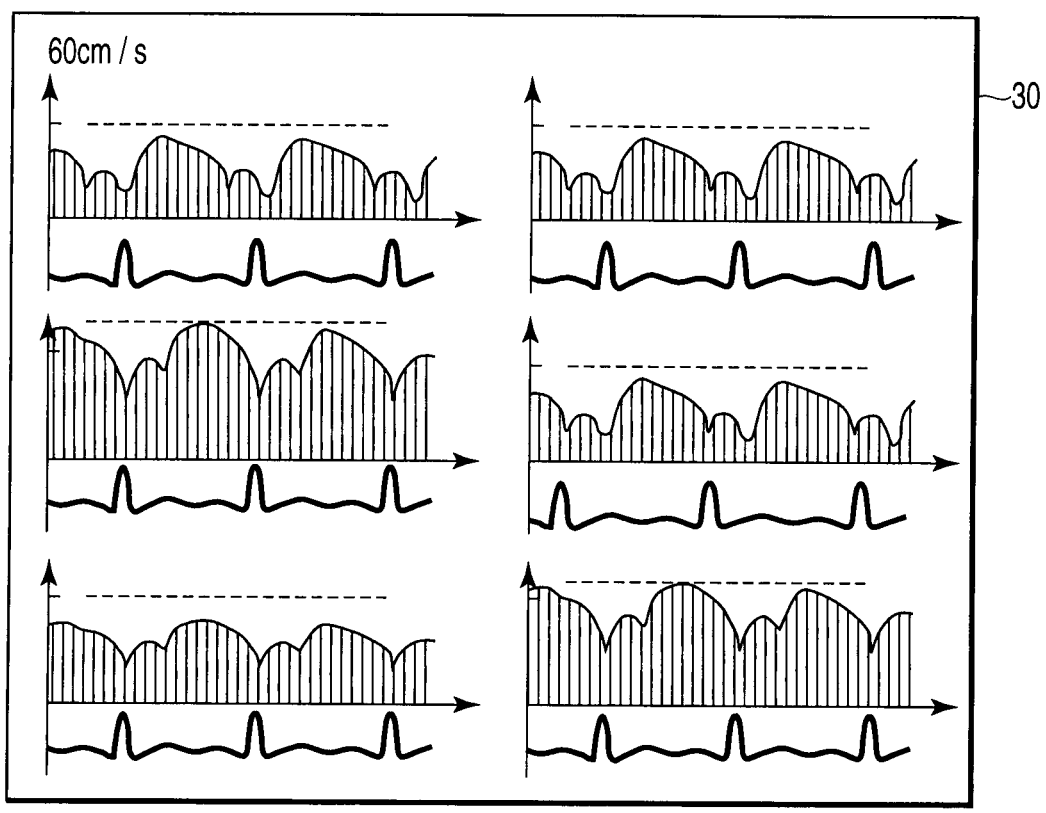
F I G. 10

ULTRASONIC DOPPLER DIAGNOSTIC APPARATUS, AND METHOD OF CONTROLLING ULTRASONIC DOPPLER DIAGNOSTIC APPARATUS

CROSS-REFERENCE TO RELATED APPLICATIONS

This application is based upon and claims the benefit of priority from prior Japanese Patent Application No. 2006-155065, filed Jun. 2, 2006, the entire contents of which are incorporated herein by reference.

BACKGROUND OF THE INVENTION

1. Field of the Invention

The present invention relates to an ultrasonic Doppler diagnostic apparatus, and more particularly, it relates to an ultrasonic Doppler diagnostic apparatus used to diagnose the function of a specimen on the basis of a change in velocity information over time within the specimen, and to a method of controlling the ultrasonic Doppler diagnostic apparatus.

2. Description of the Related Art

A coronary flow reserve is used as an index indicating the ability to increase a coronary blood flow in accordance with an increase in myocardial oxygen consumption, and is shown by a ratio of a coronary blood flow value at peak coronary dilatation to a coronary blood flow at rest. If the blockage of the blood flow is cancelled after a temporary blockage of the coronary blood flow, reactive hyperemia is shown in which coronary arterioles and capillaries distend at the maximum in response to ischemia. This ratio of the peak coronary blood flow during the reactive hyperemia to the coronary blood flow value at rest is referred to as the coronary flow reserve.

Recently, adenosine, dipyridamole, etc. have been used as coronary vasodepressors, and dobutamine, etc. have been used as sympathetic agonists, and the coronary flow reserve is evaluated from a ratio between coronary blood flow velocities before and after the load of these drugs. In the presence of coronary stenosis, peripheral coronary arteries are already distended at rest, so that a change in the coronary blood flow value is small even if the peripheral coronary arteries are maximally distended. Therefore, the coronary blood flow reserve is said to reflect the functional degree of coronary stenosis in coronary artery disease.

One of the representative methods of evaluating such a coronary flow reserve is, for example, an intravascular Doppler method as disclosed in Japanese Patent No. 2863624. However, this method is an invasive method and thus has many restrictions. Thus, transesophageal echocardiography is implemented as means for noninvasively evaluating the coronary flow reserve. Although this is a noninvasive method, the burden on a patient is too heavy. Further, owing to an improvement in the performance of ultrasonic diagnostic apparatuses, noninvasive transthoracic echocardiography has recently been the most popular method.

Here, there will be described a method of evaluating the coronary flow reserve using the transthoracic echocardiography.

First, an operator extracts a long axis view of left ventricle through apex cordis approach in a B mode, and then gradually rotates a probe counterclockwise, thus starting a scan so that right ventricle is reduced and the anterior interventricular groove is extracted. Then, the transition is made to a color mode. In the color mode, a left anterior descending coronary artery (LAD) appears and disappears outside the anterior myocardial epicardium in the vicinity of the apex of heart.

Here, if the left anterior descending coronary artery (LAD) which is displayed in a warm color during diastole is confirmed, the transition is made to a pulse Doppler (PWD) mode, and a sample volume is applied to the blood flow therein to adjust the velocity of flow using in some cases an angle correction function.

Next, the operator saves a still image of the left anterior descending coronary artery before a drug load. Then, a drug is administered, and the operator continues an inspection (ultrasonic scan) while observing that there is no abnormality in the change of condition of the patient under the drug load. After several minutes, if the operator confirms a gradual increase in the velocity of blood flow in the left anterior descending coronary artery of the patient, the operator adjusts the velocity range and base line position of the apparatus accordingly.

Furthermore, still images are periodically saved to obtain information on the peak blood flow velocity during the diastole of the left anterior descending coronary artery under the drug load. Basically, the blood flow velocity in the left anterior descending coronary artery immediately after the drug load is not different from that before the drug load, but the value of the flow velocity gradually rises with time. Once the peak blood flow velocity is registered, the value of the flow velocity gradually drops with time. After several minutes, the condition returns to the same as before the drug load.

Meanwhile, time is not constant which passes before the peak blood flow velocity is registered in the left anterior descending coronary artery after the drug load. The reason is that the time varies depending on the build, constitution, physical condition and condition of the disease of a patient, and it is impossible under the present situation for the operator to know when the patient registers the peak blood flow velocity value.

Therefore, the operator needs to frequently repeat the operation of saving still images because a current velocity waveform of the left anterior descending coronary artery being displayed on the monitor of the ultrasonic diagnostic apparatus may be registering the peak flow velocity value of the patient after the drug load. Thus, the operator continues to periodically save still images until the time when the peak flow velocity value seems to be registered (until the time when a decrease in the flow velocity value can be recognized), and then the operator terminates the inspection.

Subsequently, a plurality of still images acquired during the inspection are read from the apparatus to start the preparation for carrying out the evaluation of the coronary flow reserve.

Then, an image before the drug load as shown in FIG. 1A (an LAD blood flow waveform a, an ECG waveform b) is read and selected from within the ultrasonic diagnostic apparatus, and a blood flow velocity value is found using a measurement function. Then, a plurality of images after the drug load as shown in FIG. 1B are read, and an image is selected from those images which seems to register the peak flow velocity value, and then the peak flow velocity value is found in the same manner using the measurement function.

Next, the coronary flow reserve is found from those two data as shown in FIGS. 1A and 1B. The value of the coronary flow reserve can be found by B/A, where A is the velocity before the drug load (at rest), and B is the velocity after the drug load (at the peak flow velocity).

In general, the blood flow velocity value before the drug load remains stable, and is therefore relatively easy to select and measure in many cases. However, since the flow velocity value changes with time in the blood flow waveform after the drug load, various velocity ranges and the base lines are often set, as shown in FIGS. 2A to 2D. Therefore, as shown in FIG.

3, so much time is required and the throughput of the diagnosis is decreased in order for the operator to accurately extract an image registering the peak flow velocity value from a plurality of (N) images.

As measures to improve such a situation, for example, Jpn. Pat. Appln. KOKAI Publication No. 2005-185731 has proposed an apparatus which founds shift amounts of the velocity range and the base line in image display and changes parameters by adjusting means for the velocity range and the base line.

There is also conceived a method which uses an automatic tracing function and an automatic measurement function when finding the peak blood flow velocities in the left anterior descending coronary artery before and after the drug load. However, in most cases, although the operator thinks that he/she has captured the left anterior descending coronary artery in accordance with a pulse Doppler method, extremely strong clutter signals c from heart walls, etc. are received as shown in FIG. 4 due to the displacement of the probe from the left anterior descending coronary artery or due to cardiac motion, so that the value of the peak blood flow velocity in the left anterior descending coronary artery can not be measured but the velocity of the clutter signal is measured.

Still another method is conceived which performs multi-review display, displays acquired still images at a time, and extracts one from those still images, in order to increase the throughput of extracting an image indicating the peak flow velocity value from the plurality of still images after the drug load. However, as shown in FIG. 5, a waveform obtained in accordance with the pulse Doppler method is displayed together with a cross-sectional image in a mode such as the B mode or color mode, so that an image indicating the waveform of the flow velocity is small as such. Therefore, it is often impossible to accurately select and extract the image indicating, for example, the peak flow velocity value.

As described above, according to prior art, when evaluating the coronary flow reserve by the transthoracic echo, the operator needs to carry out scanning while observing that there is no abnormality in the change of condition of the patient under the drug load, continue the observation of the blood flow velocity value while adjusting the setting of the flow velocity range of the apparatus and the setting of the base line position, and continue to periodically take images of blood flow waveforms until a peak velocity is registered. This has been a heavy burden both emotionally and physically.

Moreover, it is impossible to evaluate the coronary flow reserve in real time, and it is necessary, after an inspection (ultrasonic scan), to read data on a plurality of images taken during the inspection (ultrasonic scan), calculate a CFR value, and evaluate the coronary flow reserve, leading to so much time required for the diagnosis of the coronary flow reserve and to a low throughput.

Methods of measuring the flow velocity value necessary for the evaluation of the coronary flow reserve include, for example, (i) a method implemented using the automatic tracing function, and (ii) a method which visually selects an image corresponding to the peak flow velocity value from a plurality of images arranged in the multi-review display and detects a velocity using the measurement function. However, these methods have problems such as lack of reliability in the accuracy of measurement due to the influence of clutter, and much time spent on the measurement of the flow velocity due to complicated operation methods.

BRIEF SUMMARY OF THE INVENTION

It is therefore an object of the present invention to provide an ultrasonic Doppler diagnostic apparatus and a method of controlling the ultrasonic Doppler diagnostic apparatus, the ultrasonic Doppler diagnostic apparatus being equipped with a coronary flow reserve evaluation support system capable of reducing a burden on an operator in evaluating a coronary flow reserve by transthoracic echo and reducing time for diagnosing the coronary flow reserve to increase throughput.

A first invention concerns an ultrasonic Doppler diagnostic apparatus provided with a display unit, the apparatus sending ultrasonic waves to a specimen, receiving a reflection signal of the ultrasonic waves from the specimen to detect a Doppler signal and obtain information on flow velocities in the specimen, and displaying the flow velocity information on the display unit, the apparatus comprising:

an adjustment unit which adjusts the flow velocity information acquired at different time points to the same velocity range; and a control unit which controls the display unit to display the flow velocity information adjusted to the same velocity range.

A second invention concerns an ultrasonic Doppler diagnostic apparatus provided with a display unit, the apparatus sending ultrasonic waves to a specimen, receiving a reflection signal of the ultrasonic waves from the specimen to detect a Doppler signal and obtain information on flow velocities in the specimen, and displaying the flow velocity information on the display unit, the apparatus comprising:

an extraction unit which extracts, in a plurality of heartbeats, a flow velocity value at one time point within one heartbeat in the flow velocity information; and a control unit which controls the display unit to draw temporal changes in a plurality of flow velocity values extracted in the plurality of heartbeats.

A third invention concerns a method of controlling an ultrasonic Doppler diagnostic apparatus, the method comprising the steps of: sending ultrasonic waves to a specimen;

receiving a reflection signal of the ultrasonic waves from the specimen to detect a Doppler signal and obtain information on flow velocities in the specimen;

displaying the flow velocity information;

adjusting the flow velocity information acquired at different time points to the same velocity range; and controlling to display the flow velocity information adjusted to the same velocity range.

A fourth invention concerns a method of controlling an ultrasonic Doppler diagnostic apparatus, the method comprising the steps of: sending ultrasonic waves to a specimen;

receiving a reflection signal of the ultrasonic waves from the specimen to detect a Doppler signal and obtain information on flow velocities in the specimen;

displaying the flow velocity information;

extracting, in a plurality of heartbeats, a flow velocity value at one time point within one heartbeat in the flow velocity information; and controlling to draw temporal changes in a plurality of flow velocity values extracted in the plurality of heartbeats.

According to the present invention, it is possible to provide an ultrasonic Doppler diagnostic apparatus and a method of controlling the ultrasonic Doppler diagnostic apparatus, the ultrasonic Doppler diagnostic apparatus being equipped with a coronary flow reserve evaluation support system capable of reducing a burden on an operator in evaluating a coronary flow reserve by transthoracic echo and reducing time for diagnosing the coronary flow reserve to increase throughput.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 1A and 1B explain a conventional ultrasonic diagnostic apparatus, wherein FIG. 1A is a diagram showing an image of a blood flow waveform before a drug load, and FIG. 1B is a diagram showing an image of a peak flow velocity value after the drug load;

FIG. 10 is a diagram showing an example of a multi-review display, on a display unit 30, of images showing the blood flow waveforms before the drug load and images of waveforms of the peak flow velocity value;

FIGS. 11A and 11B show a coronary flow peak diastole velocity curve in a left anterior descending coronary artery (LAD) in which times are plotted on a horizontal axis and flow velocity values are plotted on a vertical axis, wherein FIG. 11A is a diagram shown in real-time display with an ordinary time axis in accordance with a pulse Doppler method, and FIG. 11B is a diagram showing one data for one heartbeat on a time axis in accordance with the pulse Doppler method;

DETAILED DESCRIPTION OF THE INVENTION

Hereinafter, embodiments of the present invention will be described with reference to the drawings.

First Embodiment

First, a first embodiment of the present invention will be described.

Figure 1A:
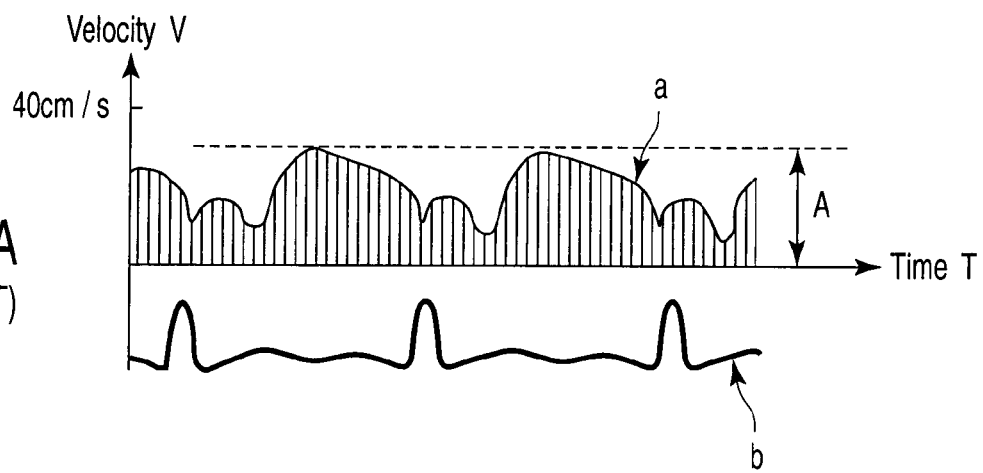
Figure 1B:
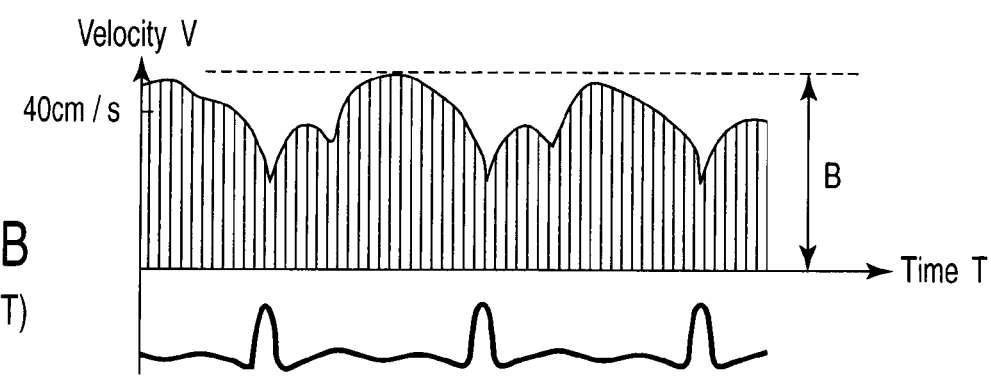
Figure 2A:
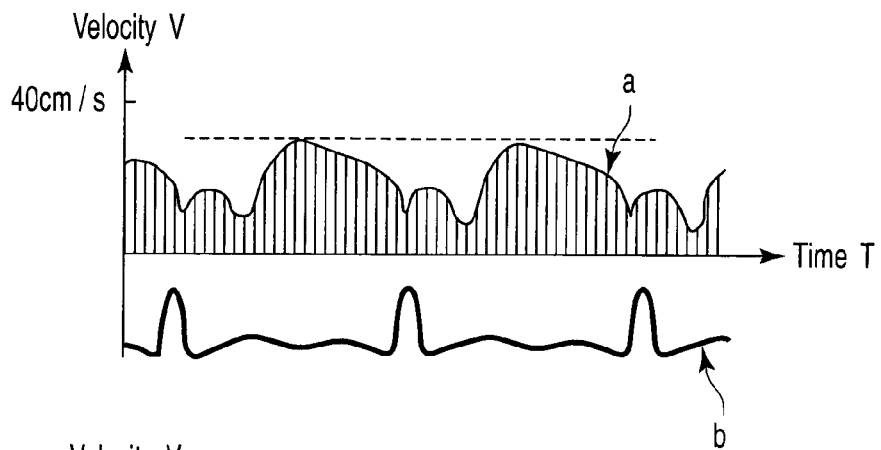
FIGS. 2A to 2D are diagrams showing a plurality of captured images of blood flow waveforms.
Figure 2B:
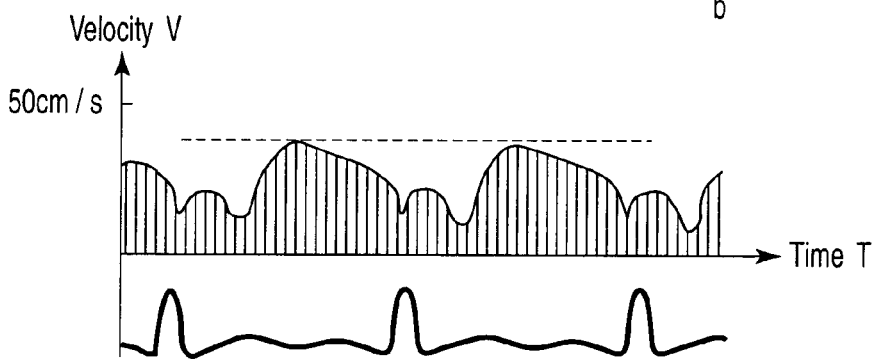
Figure 2C:
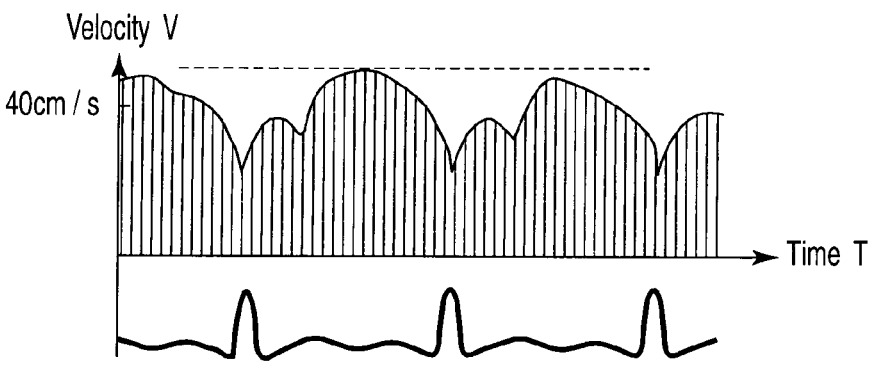
Figure 2D:
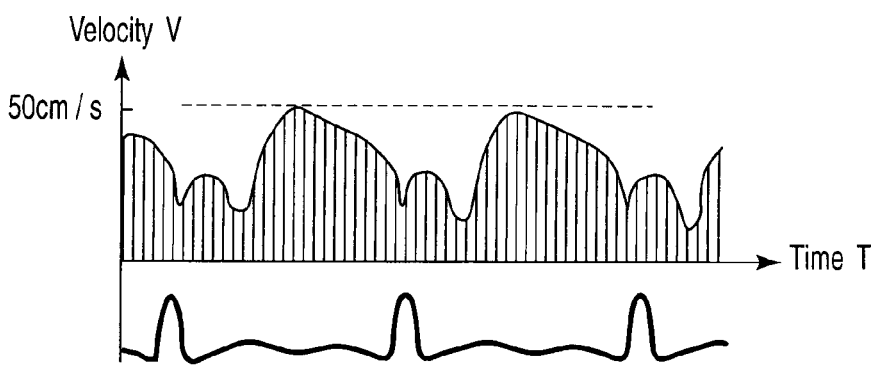
Figure 3:
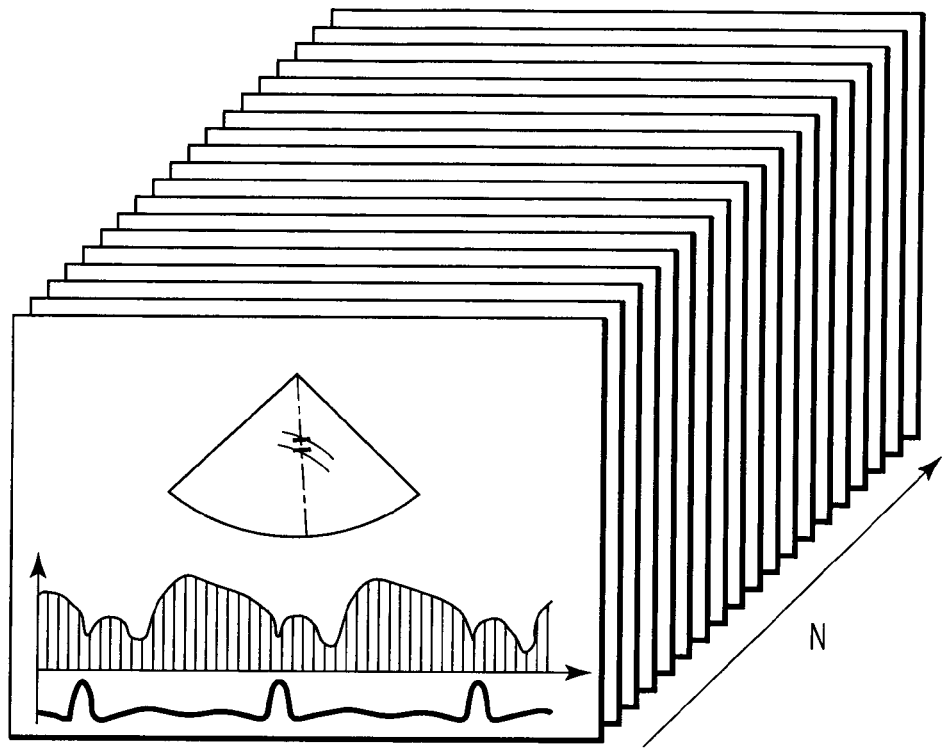
FIG. 3 explains a search method according to the conventional ultrasonic diagnostic apparatus, and is a diagram showing an example of a plurality of captured images.
Figure 4:
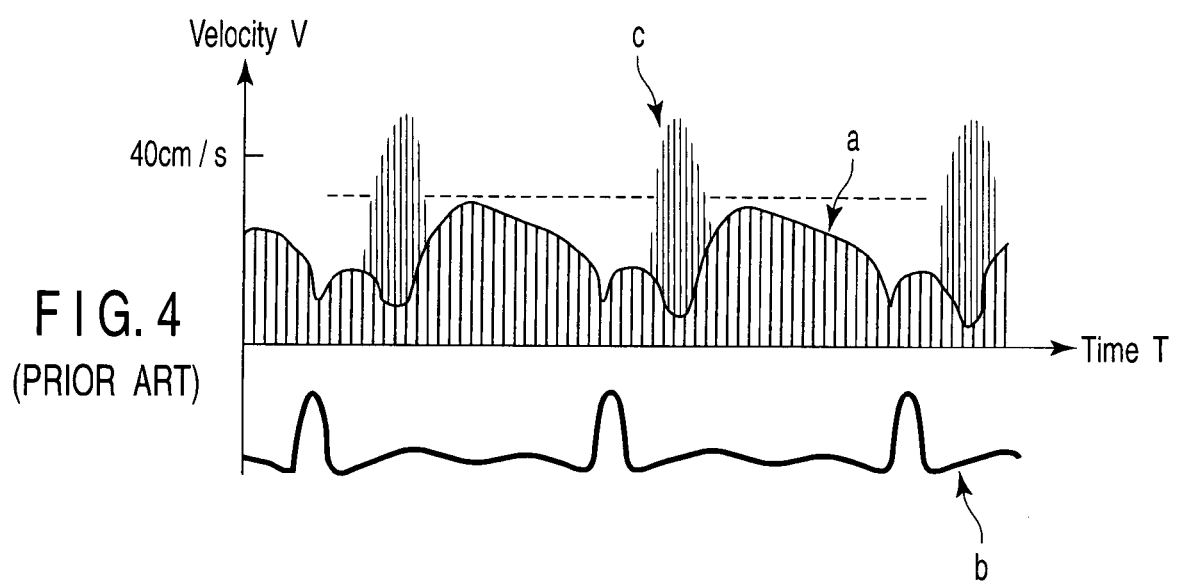
FIG. 4 is a diagram for explaining the measurement of the blood flow waveforms by a conventional automatic tracing function.
Figure 5:
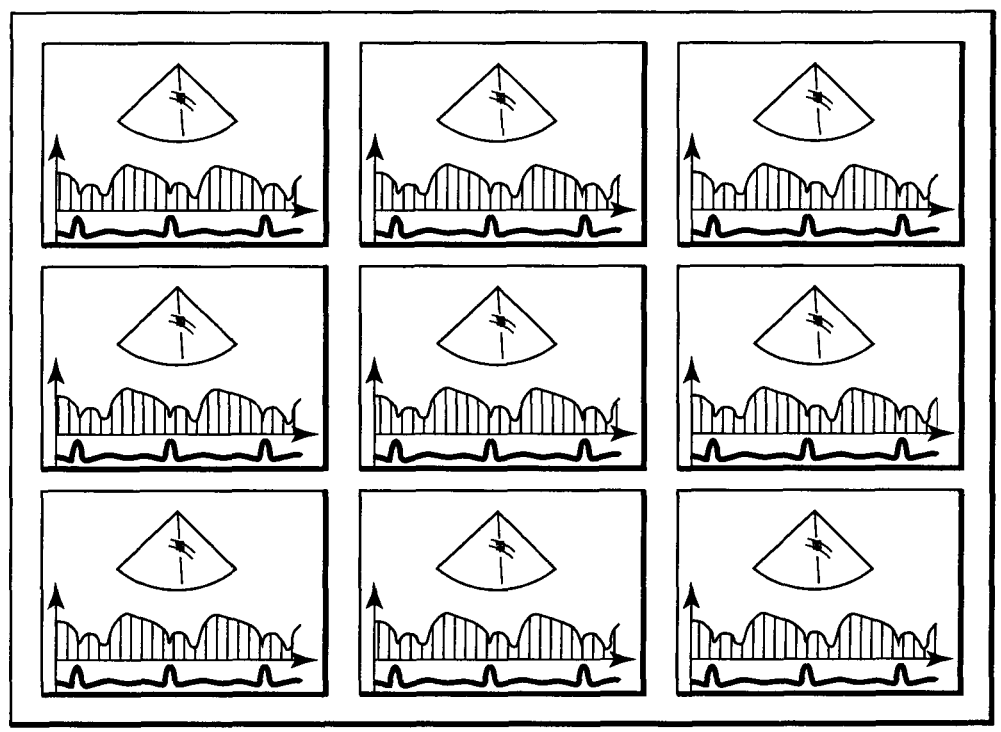
FIG. 5 is a diagram for explaining an example of the search method using a multi-review display according to the conventional ultrasonic diagnostic apparatus.
Figure 6:
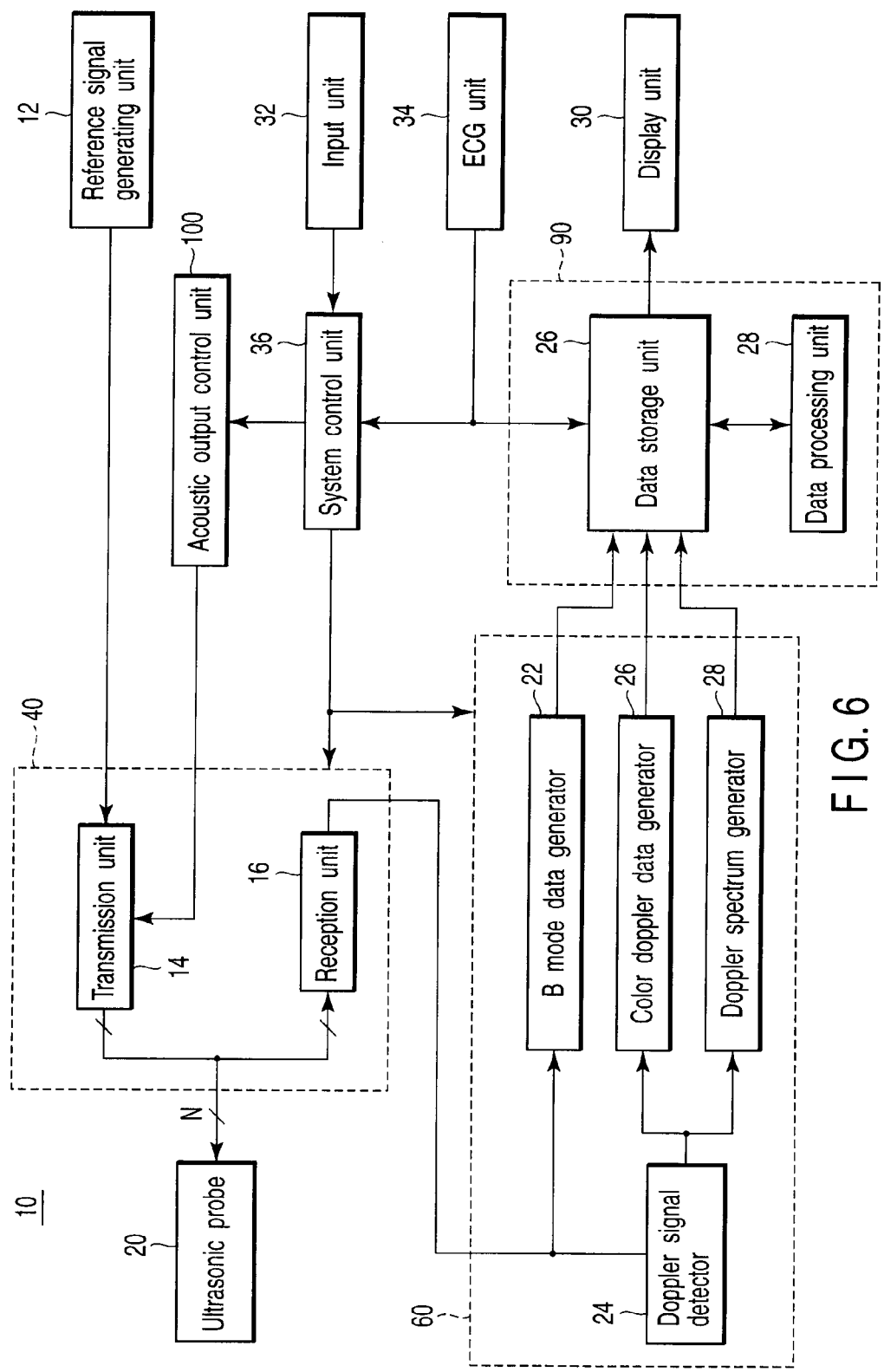
FIG. 6 is a block diagram showing the entire configuration of an ultrasonic Doppler diagnostic apparatus in a first embodiment of the present invention.
Figure 7:
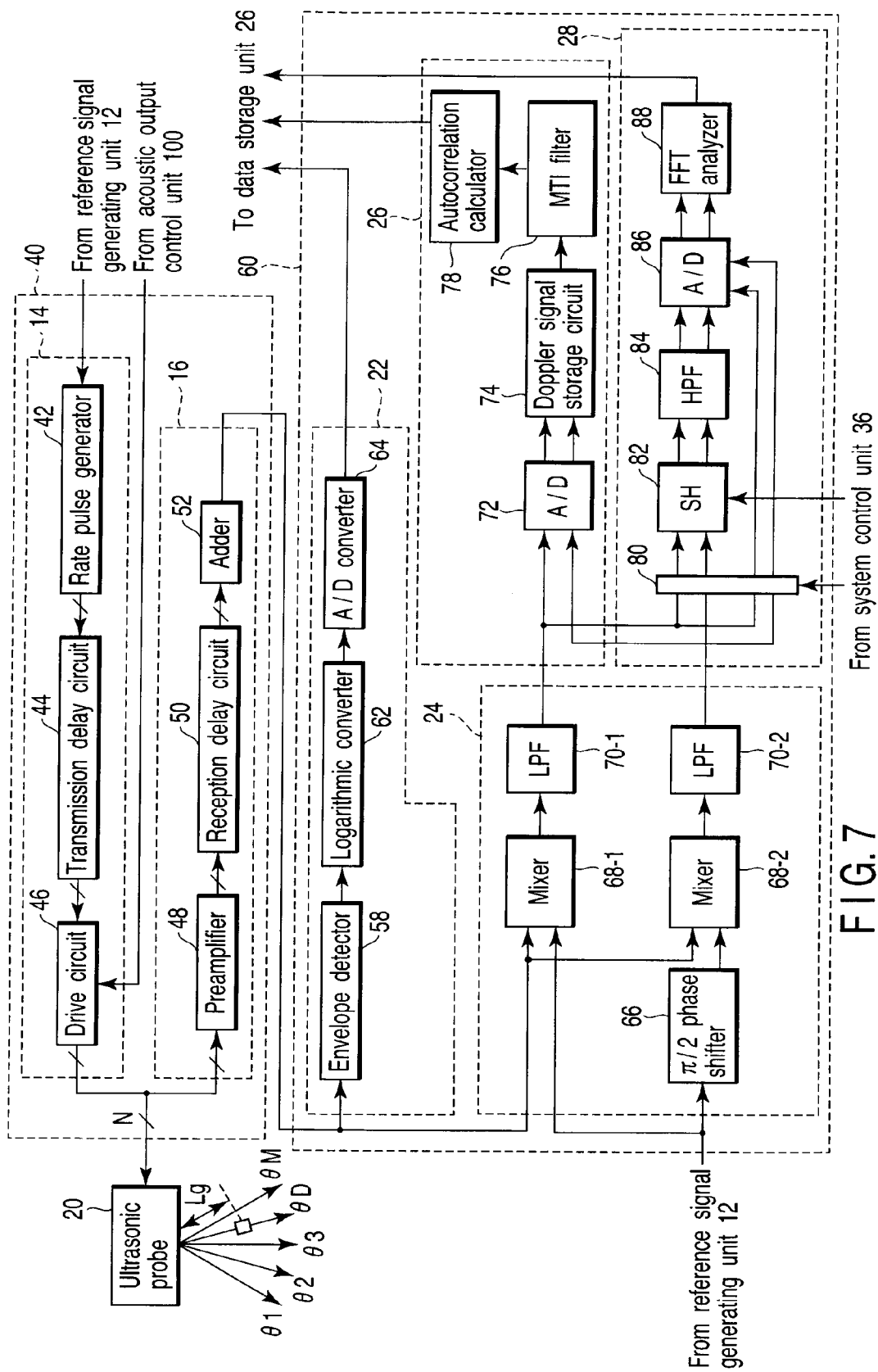
FIG. 7 is a block diagram showing the configurations of a transmission/reception unit and a data generating unit constituting the ultrasonic diagnostic apparatus in FIG. 6.

FIG. 6 is a block diagram showing the entire configuration of an ultrasonic Doppler diagnostic apparatus in the present embodiment, and FIG. 7 is a block diagram showing the configurations of a transmission/reception unit and a data generating unit constituting the ultrasonic diagnostic apparatus.

In FIG. 6, an ultrasonic Doppler diagnostic apparatus 10 comprises an ultrasonic probe 20, a transmission/reception unit 40, a data generating unit 60, a data processing/storage unit 90, and a display unit 30.

The ultrasonic probe 20 sends/receives ultrasonic waves to/from an unshown specimen. The transmission/reception unit 40 sends/receives electric signals to/from the ultrasonic probe 20. Moreover, the data generating unit 60 processes the received signal obtained from the transmission/reception unit 40, and generates B mode data, color Doppler data, and a Doppler spectrum.

The data processing/storage unit 90 saves the data generated in the data generating unit 60. The data processing/storage unit 90 also generates two-dimensional B mode image data, color Doppler image data and spectrum data, and uses this spectrum data to generate and save cine data. Further, the display unit 30 displays the B mode image data, the color Doppler image data and the spectrum data generated in the data processing/storage unit 90. As described later, the display unit 30 can also perform a multi-review display of a plurality of still images obtained in a data processing unit 28 during an inspection.

The ultrasonic Doppler diagnostic apparatus 10 also comprises an acoustic output control unit 100 for controlling transmission acoustic outputs in ultrasound tomography and an ultrasonic Doppler spectrum method, a reference signal generating unit 12, an input unit 32, and a system control unit 36. In addition, the ultrasonic Doppler diagnostic apparatus 10 is separately provided with an ECG unit 34 for collecting electrocardiographic waveforms of the specimen.

The reference signal generating unit 12 generates continuous waves having a frequency substantially equal to the center frequency of ultrasonic pulses or a frequency (fo) of ultrasonic continuous waves, or rectangular waves, for the transmission/reception unit 40 or the data generating unit 60. Specimen information, setting conditions, command signals, etc. are input to the input unit 32 by an operator. Further, the system control unit 36 performs overall control of the respective units in the ultrasonic Doppler diagnostic apparatus 10.

The ultrasonic probe 20 brings its front surface into contact with the surface of the specimen to send/receive ultrasonic waves. This ultrasonic probe 20 has at its distal end a plurality of (N) small piezoelectric vibrators one-dimensionally arranged. These piezoelectric vibrators are electric acoustic transducing elements, and have a function of transducing electric pulses or continuous waves into transmission ultrasonic waves during transmission and transducing ultrasonic reflected waves (received ultrasonic waves) into an electric signal (reception signal) during reception. This ultrasonic probe 20 has a small and light configuration, and is connected to the transmission/reception unit 40 via an unshown cable.

Furthermore, the ultrasonic probe 20 has adaptability to a sector scan, a linear scan, a convex scan, etc., and one of these scans is selected depending on a region to be diagnosed. A case will be described below where the ultrasonic probe 20 is used which is adapted to the sector scan aimed at the diagnosis of heart disease. However, the present invention is not limited to this method, and the ultrasonic probe 20 may be adapted to the linear scan or the convex scan.

The transmission/reception unit 40 shown in FIG. 7 comprises a transmission unit 14 which generates a drive signal for emitting transmission ultrasonic waves from the ultrasonic probe 20, and a reception unit 16 which receives reception ultrasonic waves from the ultrasonic probe 20.

The transmission unit 14 comprises a rate pulse generator 42, a transmission delay circuit 44 and a drive circuit 46. The rate pulse generator 42 generates rate pulses for dividing the continuous waves supplied from the reference signal generating unit 12 in order to decide a repetition cycle (Tr) of the transmission ultrasonic waves in a B mode method, a color Doppler method and a pulse Doppler method. On the other hand, the continuous waves supplied from the reference signal generating unit 12 are supplied as they are to the transmission delay circuit 44 at a subsequent stage in a continuous wave Doppler method.

The transmission delay circuit 44 provides the rate pulses or continuous waves supplied from the rate pulse generator 42 with a delay time for converging the transmission ultrasonic waves to a predetermined depth to obtain a small beam width in transmission and with a delay time for emitting the transmission ultrasonic waves in a predetermined direction. The drive circuit 46 generates a drive signal for driving the piezoelectric vibrators incorporated in the ultrasonic probe 20, on the basis of the rate pulses or continuous waves. This drive circuit 46 generates a drive signal on the basis of a control signal supplied from the acoustic output control unit 100.

On the other hand, the reception unit 16 comprises a preamplifier 48, a reception delay circuit 50 and an adder 52. The preamplifier 48 amplifies a small signal transduced to the electric signal (reception signal) by the piezoelectric vibrators, and secures an adequate S/N ratio. Further, the reception delay circuit 50 provides an output of the preamplifier 48 with a delay time for converging the reception ultrasonic waves from a predetermined depth to obtain a small reception beam width and with a delay time for setting a strong reception directivity to the reception ultrasonic waves from a predetermined direction. Then, an output of the reception delay circuit 50 provided with the predetermined delay times is sent to the adder 52 for addition and synthesis (phasing addition).

In addition, the transmission delay circuit 44 and the drive circuit 46 in the transmission unit 14, and the preamplifier 48 and the reception delay circuit 50 in the reception unit 16 generally have about the same number of independent channels as the number of piezoelectric vibrators of the ultrasonic probe 20. However, in the continuous wave Doppler method, a first piezoelectric vibrator group obtained by dividing the N piezoelectric vibrators into half, and the transmission unit 14 connected to this piezoelectric vibrator group are used for sending waves, while a remaining second piezoelectric vibrator group, and the reception unit 16 connected to this piezoelectric vibrator group are used for receiving waves.

The data generating unit 60 comprises a B mode data generator 22, a Doppler signal detector 24, a color Doppler data generator 26, and a Doppler spectrum generator 28.

The B mode data generator 22 processes a reception signal output from the adder 52 of the reception unit 16 to generate B mode data. The Doppler signal detector 24 performs quadrature detection of the reception signal to detect a Doppler signal. The color Doppler data generator 26 processes the Doppler signal detected in the Doppler signal detector 24 to generate color Doppler data. Then, the Doppler spectrum generator 28 analyses the frequency of the Doppler signal to generate a Doppler spectrum.

The B mode data generator 22 comprises an envelope detector 58, a logarithmic converter 62, and an A/D converter 64. The envelope detector 58 carries out envelope detection for a signal input to the B mode data generator 22, that is, the reception signal output from the adder 52 of the reception unit 16. The logarithmic converter 62 logarithmically converts the amplitude of a detection signal to relatively enhance weak signals. Then, the A/D converter 64 converts an output signal of the logarithmic converter 62 into a digital signal, and generates B mode data.

On the other hand, the Doppler signal detector 24 comprises a π/2 phase shifter 66, mixers 68-1 and 68-2, and LPFs (low pass filters) 70-1 and 70-2. This Doppler signal detector 24 carries out quadrature phase detection of the reception signal supplied from the reception unit 16 of the transmission/reception unit 40 by an operation described later in order to detect the Doppler signal.

Furthermore, the color Doppler data generator 26 comprises an A/D converter 72 constituted of two channels, a Doppler signal storage circuit 74, an MTI filter 76, and an autocorrelation calculator 78.

The A/D converter 72 converts Doppler signals output from the LPFs 70-1 and 70-2 in the Doppler signal detector 24, that is, analog signals subjected to the quadrature phase detection into digital signals, and saves the digital signals in the Doppler signal storage circuit 74. Then, the MTI filter 76 which is a high pass digital filter reads the Doppler signals temporarily saved in the Doppler signal storage circuit 74, and removes Doppler components (clutter components) attributed to respiratory movement, pulsating movement, etc. of organs from the Doppler signal. Moreover, the autocorrelation calculator 78 calculates an autocorrelation value for the Doppler signals from which blood flow information alone has been extracted by the MTI filter 76, and further calculates an average velocity value, variance value, etc. of the blood flow on the basis of the autocorrelation value.

On the other hand, the Doppler spectrum generator 28 comprises a switching circuit 80, a sample hold circuit (SH) 82, a high pass filter (HPF) 84, an A/D converter 86, and an FFT analyzer 88. The color Doppler data generator 26 carries out an FFT analysis for the Doppler signal obtained in the Doppler signal detector 24.

In addition, each of the SH 82, the HPF 84 and the A/D converter 86 is constituted of two channels, and complex components of the Doppler signal output from the Doppler signal detector 24, that is, actual components (I components) and virtual components (Q components) are supplied to each channel.

The data processing/storage unit 90 comprises a data storage unit 26 and a data processing unit 28. The data storage unit 26 sequentially saves the B mode data, the color Doppler data, and the Doppler spectrum generated per scanning direction in the data generating unit 60, and then generates two-dimensional B mode image data, color Doppler image data and spectrum data. Further, the spectrum data is used to save cine data generated by the data processing unit 28.

On the other hand, the data processing unit 28 performs image processing and scan conversion for the B mode image data and the color Doppler image data, generates trace data for the peak frequency components of the spectrum data, and processes data, etc. generated by the control of the acoustic output control unit 100. Further, the data processing unit 28 performs processing to erase the display of cross-sectional images in the modes such as the B mode and color modes which are unnecessary in the evaluation of the coronary flow reserve, and processing to only extract waveforms obtained in accordance with the pulse Doppler method. Such processing is performed to quickly extract an image showing the peak flow velocity value from a plurality of still images acquired during the inspection. In addition, all the images saved in the data storage unit 26 during the inspection are processed for the multi-review display of these images on the display unit 30 after the values of velocity ranges and the base line positions of these images are uniformed.

Next, the operation of the ultrasonic Doppler diagnostic apparatus in the first embodiment of the present invention will be described with reference to a flowchart in FIG. 8.

First, in step S1, the operator places the ultrasonic probe 20 on the specimen, and extracts a long axis view of left ventricle through apex cordis approach in a B mode, and then gradually rotates the probe counterclockwise, thus starting a scan so that right ventricle is reduced and the anterior interventricular groove is extracted. Then, in step S2, the transition is made to a color mode. In the color mode, the presence of a left anterior descending coronary artery (LAD) is confirmed which appears and disappears outside the anterior myocardial epicardium in the vicinity of the apex of heart and which is displayed in a warm color during diastole.

Subsequently, in step S3, the transition is made to a pulse Doppler (PWD) mode, and the waveform of the left anterior descending coronary artery is confirmed. Then, in subsequent step S4, a sample volume is applied to the blood flow therein to adjust the velocity of flow using in some cases an angle correction function. Further, in step S5, the operator saves (captures) a still image of the left anterior descending coronary artery before a drug load (at rest) by the operation and setting with the input unit 32. Thus, the still image is saved in the data storage unit 26.

Then, a drug is administered in step S6, and the operator continues an inspection (ultrasonic scan) while observing that there is no abnormality in the change of condition of the patient under the drug load. After several minutes, the operator confirms on the display unit 30 a gradual increase in the velocity of blood flow in the left anterior descending coronary artery of the patient, in step S7. Then, in step S8, the operator adjusts the velocity range and base line position of the apparatus to a desired velocity range and base line position accordingly, through operation and input from the input unit 32.

Next, in step S9, still images are periodically saved in the data storage unit 26 to obtain information on the peak blood flow velocity during the diastole of the left anterior descending coronary artery under the drug load. Basically, the blood flow velocity in the left anterior descending coronary artery immediately after the drug load is not different from that before the drug load, but the value of the flow velocity gradually rises with time. Once the peak blood flow velocity is registered, the value of the flow velocity gradually drops with time. After several minutes, the condition returns to the same as before the drug load.

Depending on the build, constitution, physical condition and condition of the disease of a patient, there are variations in time before the peak blood flow velocity in the left anterior descending coronary artery after the drug load is registered. It is therefore impossible under the present situation for the operator to know when the patient registers the peak blood flow velocity. Therefore, at present, the operator needs to frequently repeat the operation of saving still images because a current velocity waveform of the left anterior descending coronary artery being displayed on the display unit 30 of the ultrasonic diagnostic apparatus may be registering the peak flow velocity value of the patient after the drug load. If this operation is neglected, an accurate evaluation of the coronary flow reserve may be precluded because it is impossible to register the peak flow velocity value in the left anterior descending coronary artery of the patient after the drug load.

Therefore, in step S10, the operator continues to periodically save still images until the time when the peak flow velocity value seems to be registered (until the time when a decrease in the flow velocity value can be recognized). Then, the operator terminates the inspection in step S11. Subsequently, in step S12, a plurality of still images acquired during the inspection are read from the data storage unit 26 to start the preparation for carrying out the evaluation of the coronary flow reserve.

Next, in step S13, Doppler image parts alone are trimmed in the data processing unit 28 from all of the (N) images saved in the data storage unit 26 in step S5 (before the drug load) and in step S9 (under the drug load), and then the velocity ranges and the base line positions of these images are adjusted to common levels. For example, the images are adjusted by bringing different velocity ranges 30 cm/s, 40 cm/s, 50 cm/s and 60 cm/s as shown in FIG. 9A to the maximum velocity range 60 cm/s as shown in FIG. 9B, and the multi-review display of these images are shown on the display unit 30.

Then, in steps S14 and S15, the operator visually searches for an image indicating a waveform of the blood flow velocity before the drug load and an image indicating a waveform of the peak flow velocity value from a plurality of images displayed in the form of the multi-review on the display unit 30 as shown in FIG. 10 as a result of step S13. Subsequently, in step S16, a known measurement function in the ultrasonic Doppler diagnostic apparatus 10 is used to measure the peak diastole velocity with regard to the two images selected in steps S14 and S15. Then, in step S17, the coronary flow reserve (CFR) is found from the peak flow velocity value before the drug load and the peak flow velocity value after the drug load that have been obtained as described above. Then, the present sequence terminates.

Thus, according to the first embodiment, the display of cross-sectional images in the modes such as the B mode and color modes which are unnecessary in the evaluation of the coronary flow reserve is erased, and a plurality of images obtained in accordance with the pulse Doppler method can be displayed in a large display area at a time, thereby making it possible to reduce the time of ascertaining which flow velocity is higher.

Figures 9A, 9B:
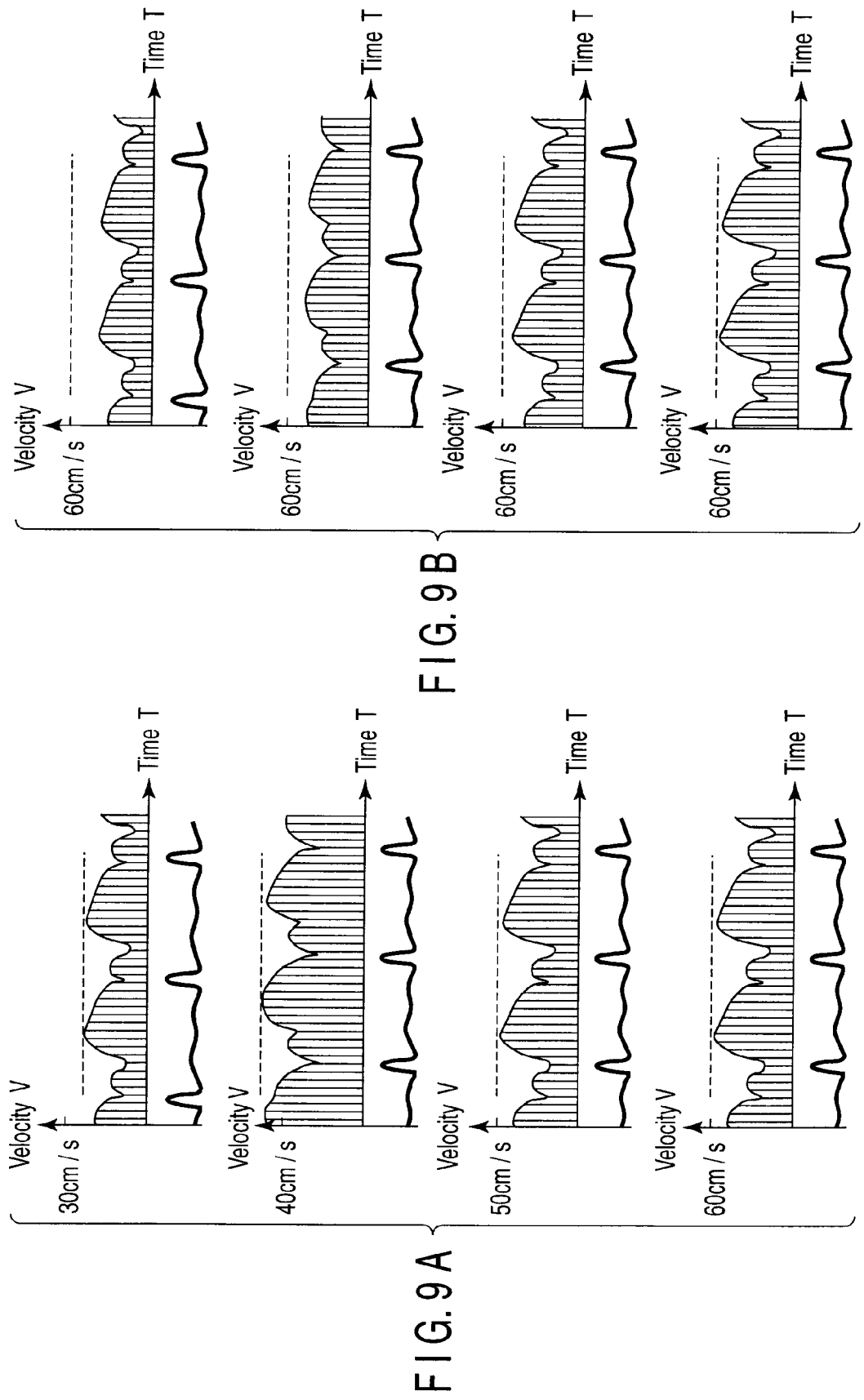
FIGS. 9A and 9B are diagrams explaining an example in which a plurality of captured images obtained by the ultrasonic Doppler diagnostic apparatus in the first embodiment of the present invention are displayed so that velocity ranges of these images are adjusted to a uniform velocity range.

In addition, an example has been shown in the captured images in FIGS. 9A and 9B in which the velocity ranges are adjusted to the uniform velocity range. However, it should be understood that the adjusted images can be similarly displayed in the case of adjusting the base line positions or adjusting both the velocity ranges and the base line positions.

Second Embodiment

Next, a second embodiment of the present invention will be described.

In the first embodiment, the display unit 30 only displays a locus curve in a time direction of the peak flow velocity value at every heartbeat of the blood flow in the left anterior descending coronary artery. However, in the second embodiment, the locus curve is displayed in real time on the display unit 30 together with image displays in a B mode, a color mode and a PWD mode in order to increase the throughput of the whole inspection when the coronary flow reserve (CFR) is found.

In addition, the basic configuration and operation of the ultrasonic Doppler diagnostic apparatus 10 in the second embodiment described below are the same as those in the first embodiment described above, so that the same reference numerals are assigned to the same parts to avoid the repetition of explanation, and different parts alone will be described while the same parts are neither shown in the drawings nor described.

Figures 11A, 11B:
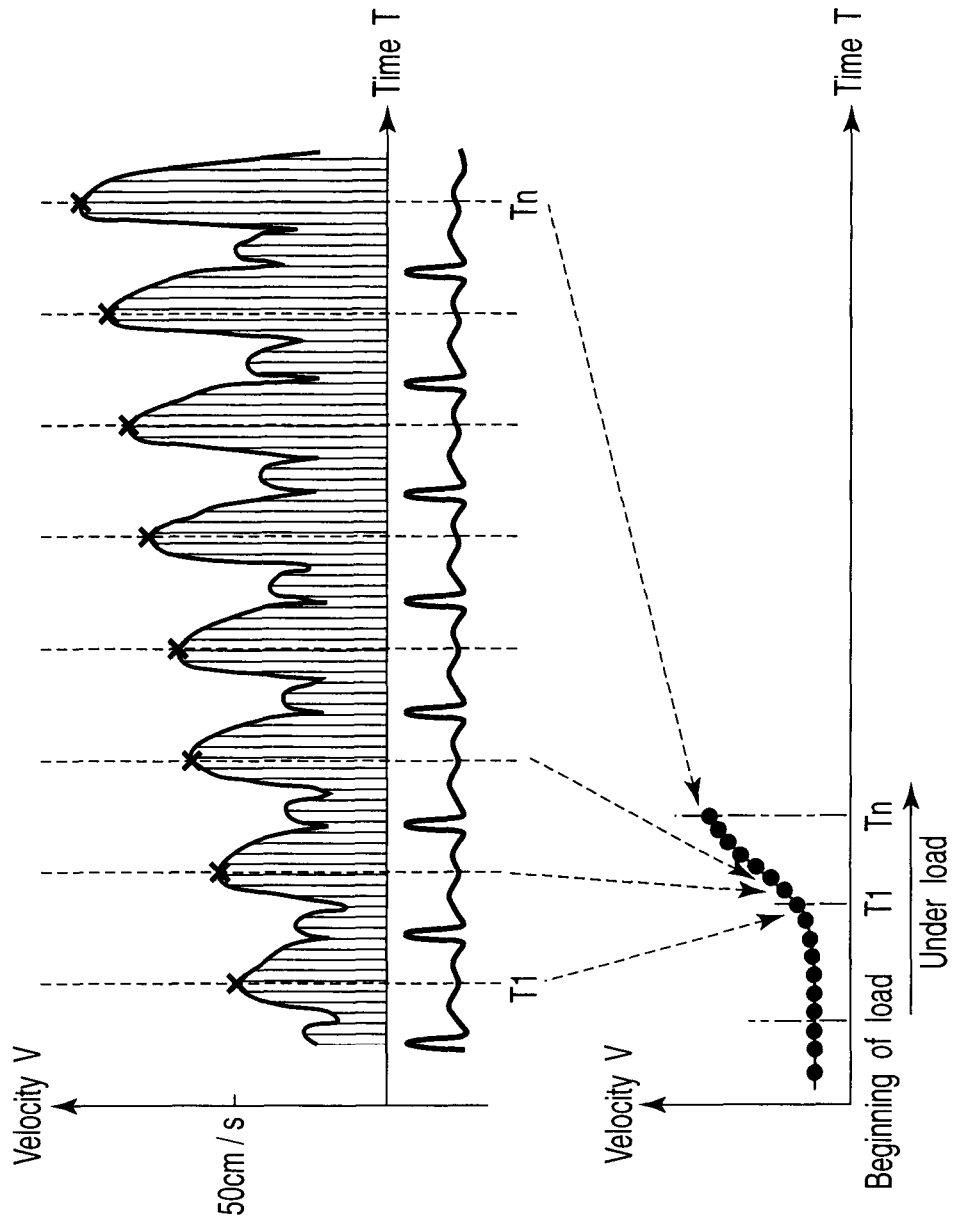

FIGS. 11A and 11B show a coronary flow peak diastole velocity curve in the left anterior descending coronary artery (LAD) in which times are plotted on a horizontal axis and flow velocity values are plotted on a vertical axis, wherein FIG. 11A is a diagram shown in real-time display with an ordinary time axis in accordance with a pulse Doppler method, and FIG. 11B is a diagram showing one data for one heartbeat on a time axis in accordance with the pulse Doppler method.

The scale of the time axis of the locus curve shown in FIG. 11B only allows one data to be obtained for one heartbeat, and is therefore significantly different from the scale of the time axis indicated in accordance with the ordinary pulse Doppler method shown in FIG. 11A. In other words, black circles on the curve shown in FIG. 11B correspond to crosses on the curve shown in FIG. 11A.

In addition, the locus curve as shown in FIG. 11B is referred to here as a coronary flow peak diastole velocity curve.

According to this coronary flow peak diastole velocity curve, it is possible to know the tendency of change in the peak flow velocity value at every heartbeat in the left anterior descending coronary artery (LAD) after the drug load. Therefore, by taking a look at the tendency of the curve, it is possible to instantly judge whether or not the flow velocity value in the left anterior descending coronary artery (LAD) of the patient after the drug load has already reached its peak.

It is known that this locus curve has the following characteristics: the locus curve shows a substantially steady-state flow velocity value before a drug load, and the curve shows a gradual rise when several minutes has passed after the drug load, and the locus remains substantially flat in the vicinity of a point at which the peak flow velocity value is obtained, and then the curve shows a fall. If the locus curve is rising, it means that the peak flow velocity value has not been reached, so that a scan still needs to be continued. On the contrary, if the locus curve is falling, it is possible to judge that the peak flow velocity value has already been passed. This shows that the evaluation of the coronary flow reserve (CFR) is possible whenever the scan is interrupted. For example, the curve shown in FIG. 11B is still rising at current time Tn, and this therefore means that the peak flow velocity value has not been reached.

Next, the operation of the ultrasonic Doppler diagnostic apparatus in the second embodiment of the present invention will be described with reference to a flowchart in FIG. 12.

Figure 8:
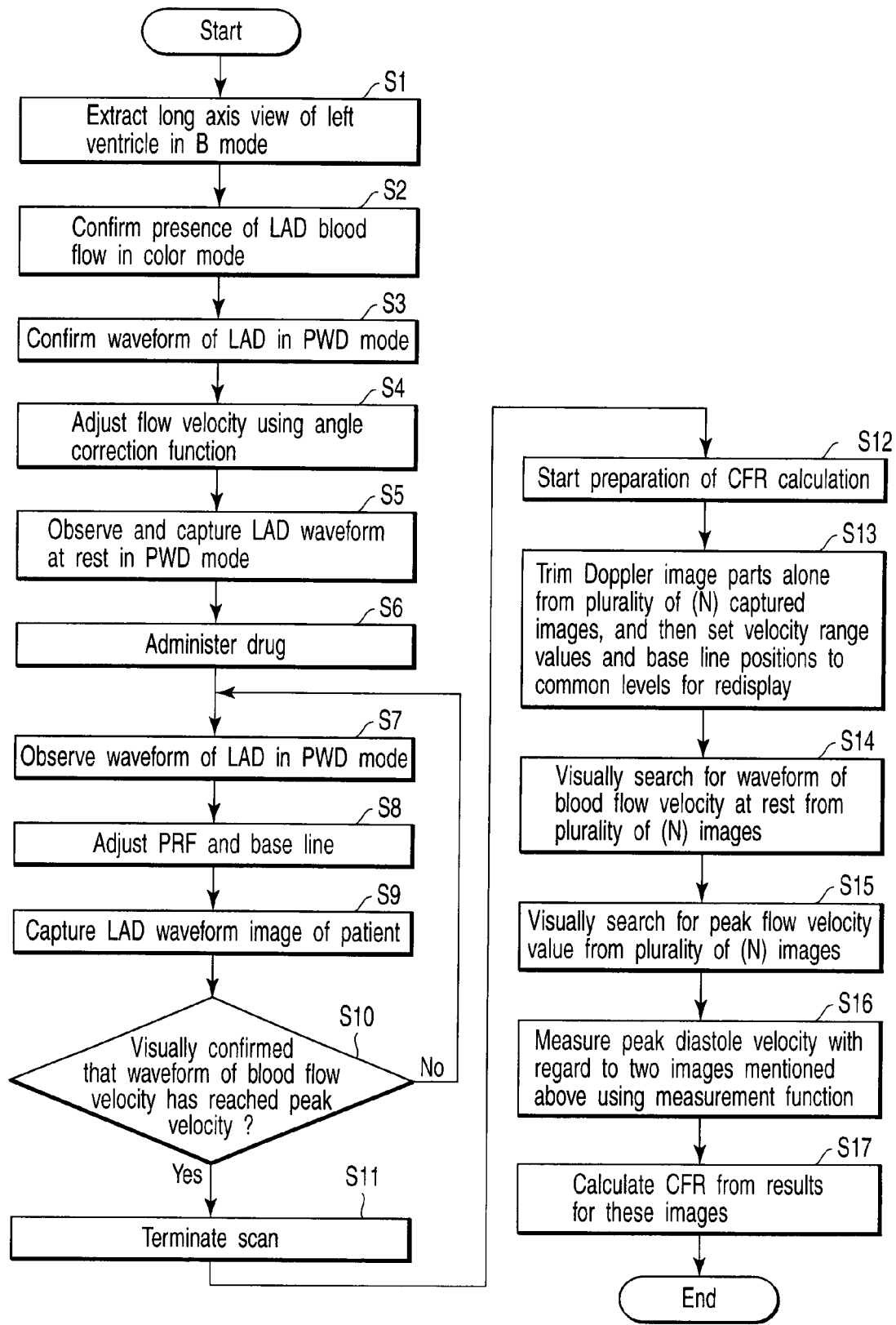
FIG. 8 is a flowchart explaining the operation of the ultrasonic Doppler diagnostic apparatus in the first embodiment of the present invention.
Figure 12:
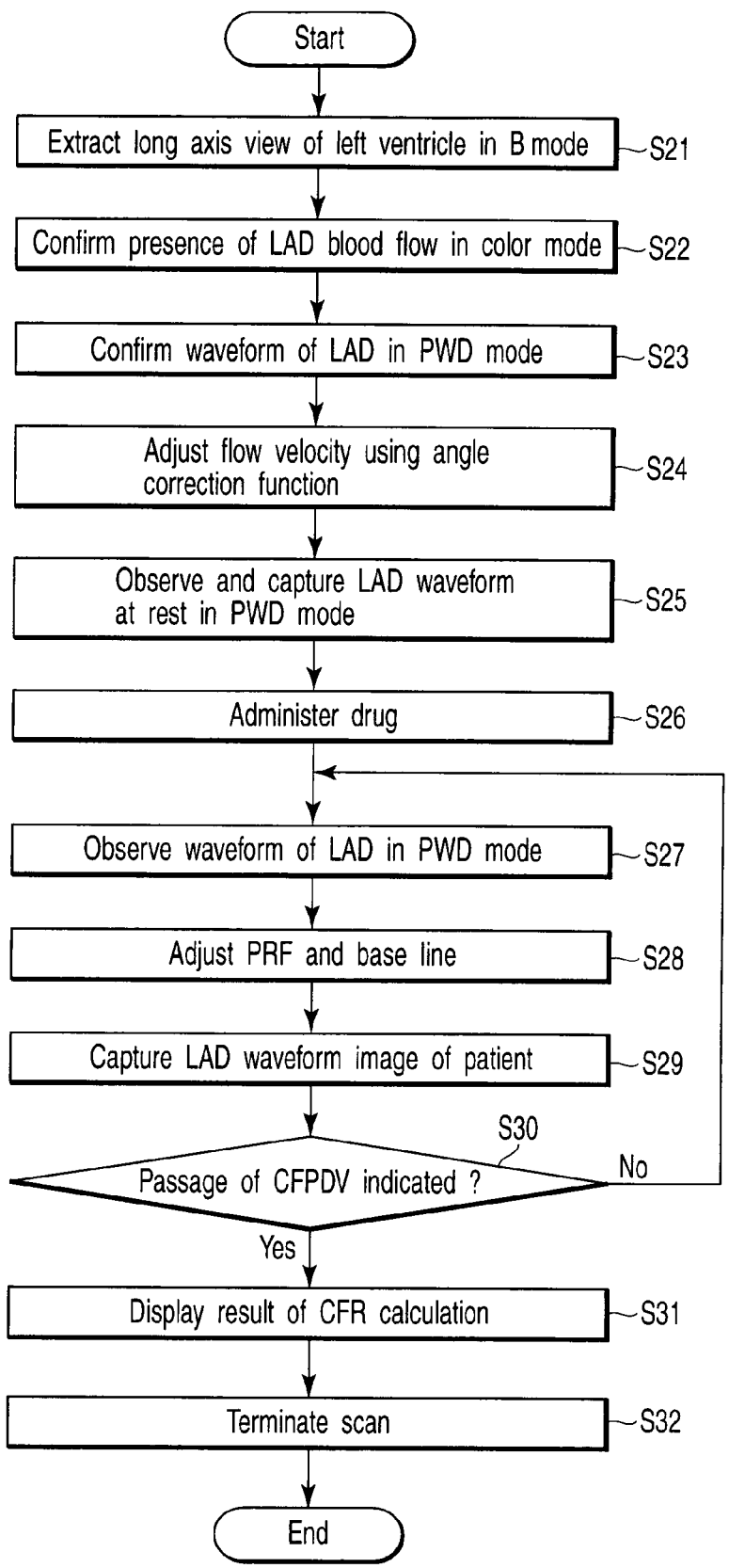
FIG. 12 is a flowchart explaining the operation of the ultrasonic Doppler diagnostic apparatus in a second embodiment of the present invention.

In addition, steps S21 to S29 in the flowchart in FIG. 12 are the same as steps S1 to S9 in the flowchart in FIG. 8 in the first embodiment described above. Therefore, steps S21 to S29 are not described here by referring to the corresponding step numbers.

Figure 13:
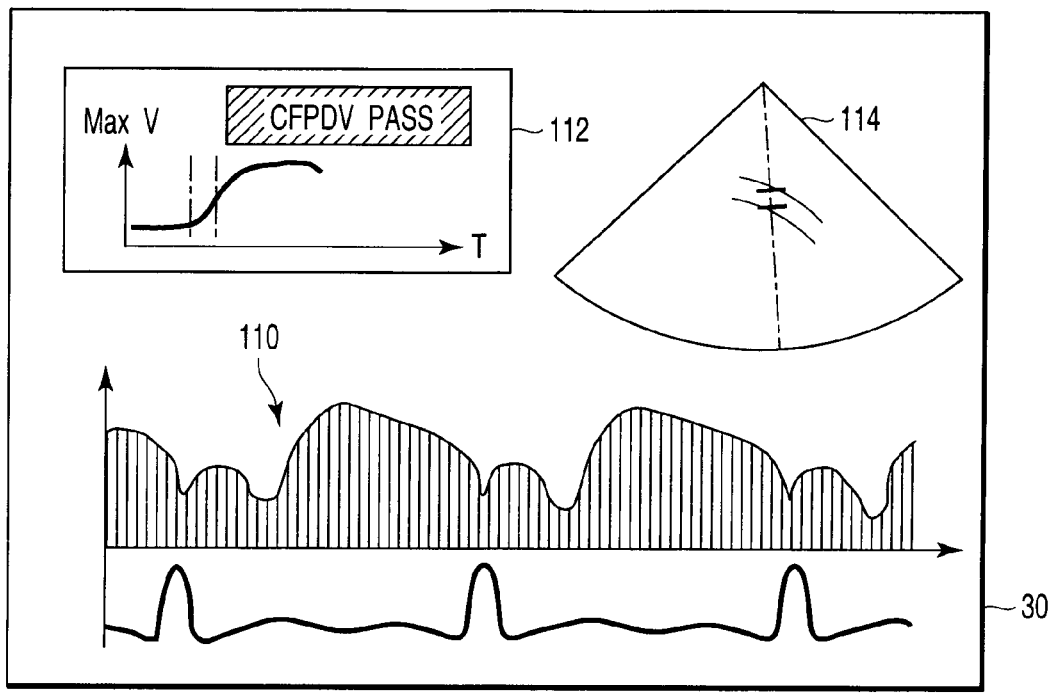
FIG. 13 is a diagram showing an example in which the display unit 30 displays a screen 110 for a real-time locus curve including an ECG waveform, a display screen 112 for the whole locus curve, and a display screen 114 for a left anterior descending coronary artery targeted for inspection.

Now, as shown in FIG. 13, the display unit 30 displays a screen 110 for a real-time locus curve including an ECG waveform, a display screen 112 for the coronary flow peak diastole velocity curve, and a display screen 114 for a left anterior descending coronary artery targeted for inspection. On the display screen 112, if the peak flow velocity value changes from a rising state to a falling state, it is judged that the peak flow velocity value has already been reached.

Figure 14:
FIG. 14 is a diagram showing an example of a caution mark 118 such as "CFPDV PASS" indicating that the peak flow velocity value has been reached.

Therefore, a caution mark (message) 118 such as "CFPDV PASS" as shown in FIG. 14 indicating that the peak flow velocity value has been reached may be shown in the display screen 112 to provide the operator with the information. That is, whether the passage of the CFPDV has been indicated is judged in step S30. Here, if the indication of the passage has not been given yet, the transition is made to step S27 to repeat the observation described above. On the other hand, if the passage indication 118 is given, the transition is made to step S31. Then, in step S31, the above-mentioned calculation of the coronary flow reserve (CFR) is carried out, and the result of the calculation is displayed. Subsequently, the scan is terminated in step S32.

The locus and notification are displayed in such a manner together with the displays in the B mode, the color mode and the PWD mode, so that the operator can evaluate the coronary flow reserve in a simple and easy manner without looking away from the screen of the display unit 30 on which the operator is observing the ordinary pulse Doppler waveform. Moreover, it is possible to prevent much waste of time which has hitherto been produced to find the peak flow velocity value from a plurality of still images after completion of the scan.

In order to obtain one data for one heartbeat to draw this locus curve, it is only necessary to acquire data after delayed by Δt time using any one of P waves, Q waves, R waves, S waves and T waves of an ECG signal as a trigger. In order to decide a delay time, a delay time can be set in a steady state before a drug load, and the same setting of the delay time can also be applied after the drug load. While FIGS. 11A and 11B are explained above using the ECG signal, other biological signals may be used as the trigger signals.

Figure 15:
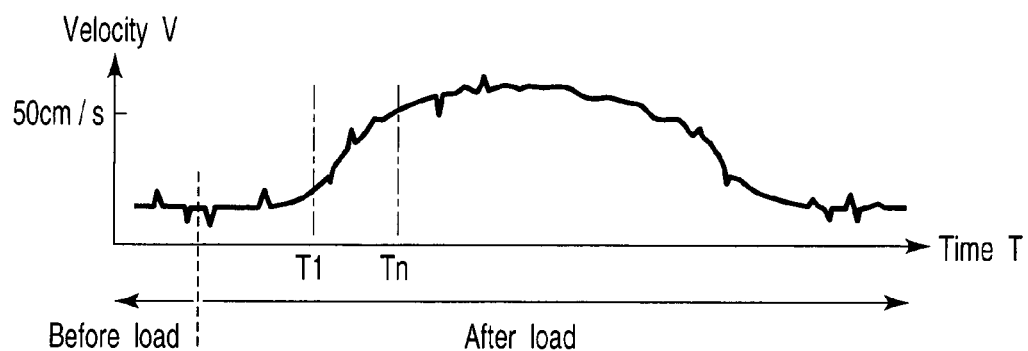
FIG. 15 is a diagram showing one example of a coronary flow peak diastole velocity curve.
Figure 16:
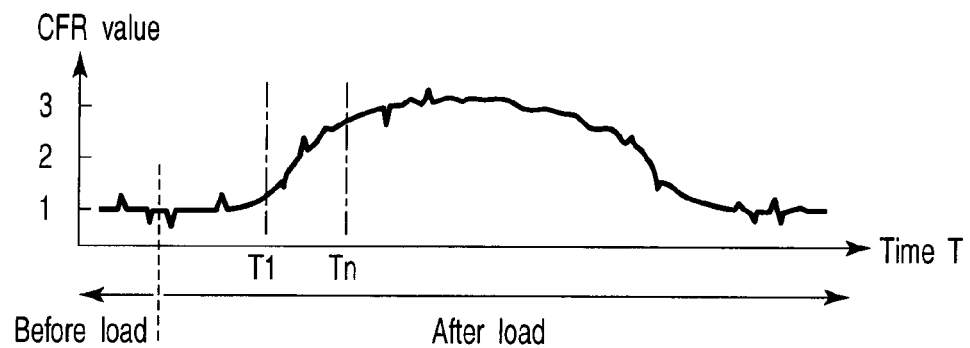
FIG. 16 is a diagram showing a locus curve of a coronary flow reserve (CFR) in a time direction, which indicates a ratio of the peak flow velocity value at every heartbeat of the moment to the flow velocity value in a steady state before the drug load in FIG. 15.

FIG. 15 is a diagram showing one example of a coronary flow peak diastole velocity curve. FIG. 16 shows a locus curve of the coronary flow reserve (CFR) in the time direction, which indicates a ratio of the peak flow velocity value at every heartbeat of the moment to the flow velocity value in a steady state before the drug load in FIG. 15. This locus curve of the coronary flow reserve may be displayed in real time together with image displays in the B mode, the color mode and the PWD mode.

Figure 17:
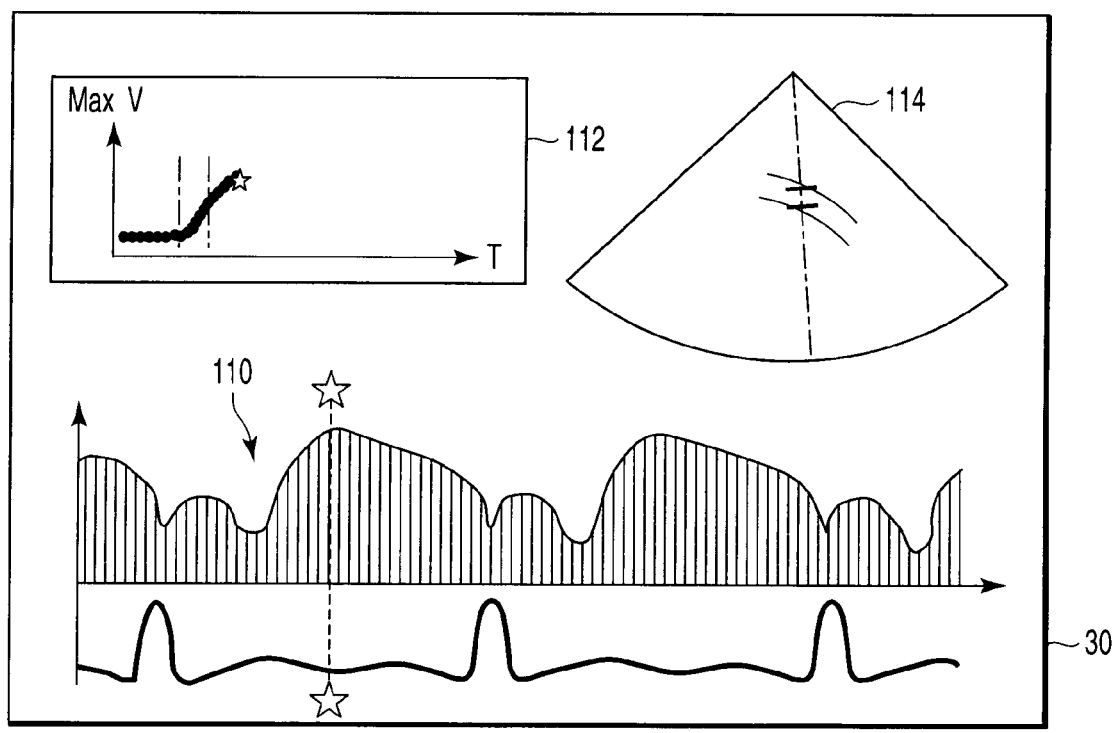
FIG. 17 is a diagram showing one example in which the coronary flow peak diastole velocity curve is displayed together with image displays in a B mode, a color mode and a PWD mode.

FIG. 17 is a diagram showing one example in which the coronary flow peak diastole velocity curve is displayed together with the image displays in the B mode, the color mode and the PWD mode. In FIG. 17, the locus curve in the display screen 112 is still rising, so that it can be judged that the peak flow velocity value has not been reached.

Figure 18:
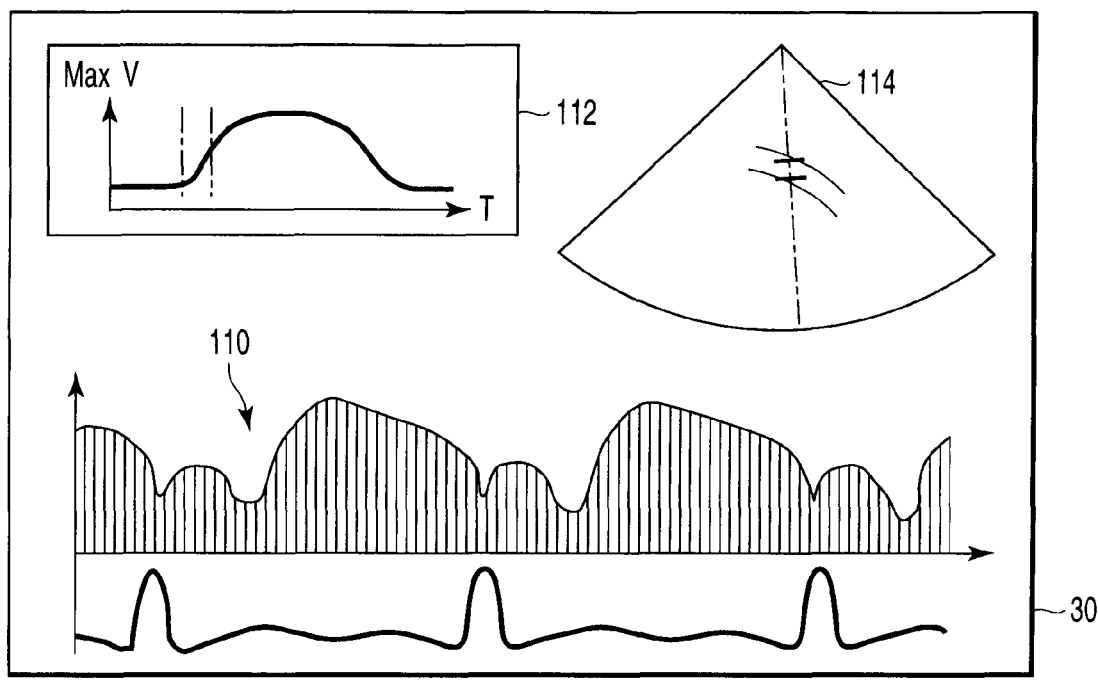
FIG. 18 is a diagram showing an example of a state (state where an ultrasonic scan has been terminated) after several minutes have passed from the state of the screen display shown in FIG. 17.

FIG. 18 is a diagram showing an example of a state (state where the ultrasonic scan has been terminated) after several minutes have passed from the state of the screen display shown in FIG. 17. The state in FIG. 18 shows that there is no longer any change in the flow velocity due to the administration of the drug.

Figure 19:
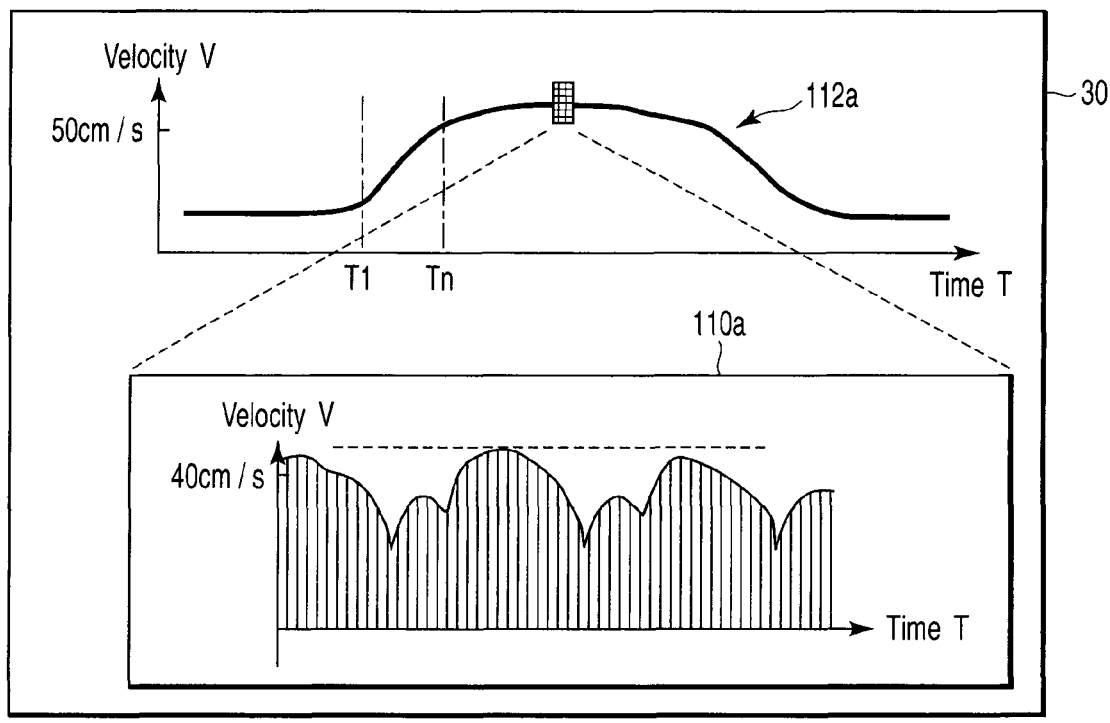
FIG. 19 is a diagram showing an example of a state after completion of the scan displayed in a magnified form.

FIG. 19 is a diagram showing an example of a state after completion of the scan displayed in a magnified form. This shows that a pointer is moved onto a coronary flow peak diastole velocity curve 112a by the input unit 32 such that an image 110a corresponding to the time indicated by the pointer is read onto the screen of the display unit 30 from moving images saved in the data storage unit 26 on the apparatus. This is carried out under the control of the system control unit 36. Since the display of the locus of the coronary flow peak diastole velocity curve is a function of guidance for the measurement of the coronary flow reserve, the function of rereading and displaying the image by the indication of the pointer as described above is particularly effective in detailed checking after completion of the inspection (ultrasonic scan).

Figure 20:
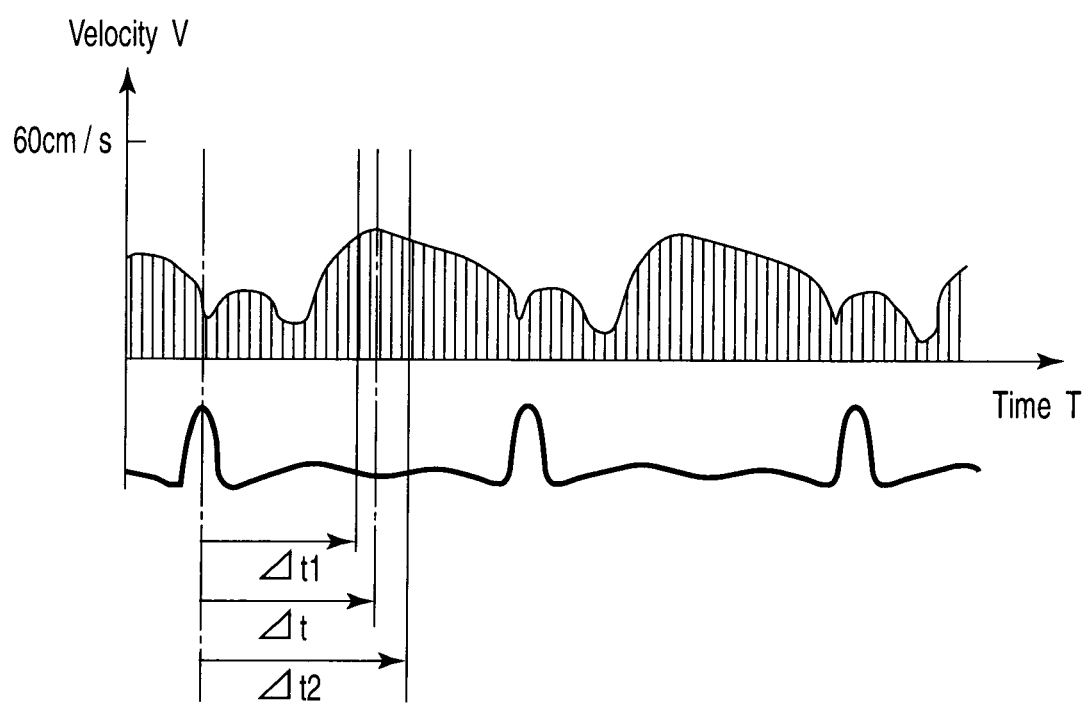
FIG. 20 is a diagram showing an example of acquiring a flow velocity value at a time delayed by Δt time using R waves as a trigger when an ECG signal is used.

FIG. 20 is a diagram showing an example of acquiring a flow velocity value at a time delayed by $\Delta t$ time using the R waves as a trigger when the ECG signal is used. Actually, the place delayed by $\Delta t$ time does not necessarily correspond to the peak flow velocity value due to, for example, fluctuations in heartbeats of the patient, so that the coronary flow peak diastole velocity curve may be drawn using a method of acquiring the peak flow velocity value from the R waves between $\Delta t1$ time and $\Delta t2$ time.

Thus, the locus curve in the time direction of the peak flow velocity value at every heartbeat of the blood flow in the left anterior descending coronary artery is displayed in real time together with the image displays in the B mode, the color mode and the PWD mode in order to increase the throughput of the whole inspection when the coronary flow reserve is found, so that it is possible to know in real time the tendency of change in the peak flow velocity value at every heartbeat in the left anterior descending coronary artery after the drug load. Therefore, by taking a look at the tendency of the curve, it is possible for the operator to instantly judge whether or not the flow velocity value in the left anterior descending coronary artery of the patient after the drug load has already reached its peak.

While the embodiments of the present invention have been described above, the present invention is not limited to the embodiments described above, and various modification can be made without departing from the spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic Doppler diagnostic apparatus provided with a display unit, the apparatus sending ultrasonic waves to a specimen, receiving a reflection signal of the ultrasonic waves from the specimen to detect a Doppler signal and obtain information on flow velocities in the specimen, and displaying the flow velocity information on the display unit, the apparatus comprising:

a trimming unit configured to trim a first flow velocity information acquired at a first time period of different time points and a second flow velocity information acquired at a second time period of different time points from the information on the flow velocities;

an adjustment unit which adjusts the first flow velocity information to a same velocity range, and adjusts the second flow velocity information to the same velocity range; and a control unit which controls the display unit to simultaneously display the first flow velocity information and the second flow velocity information adjusted and trimmed to the same velocity range.

2. The ultrasonic Doppler diagnostic apparatus according to claim 1, wherein the adjustment unit further adjusts velocity ranges of blood flow velocity information acquired at time points before and after an administration of a drug to the specimen.

3. The ultrasonic Doppler diagnostic apparatus according to claim 2, wherein the adjustment unit further adjusts base line positions of the flow velocity information before and after the administration of the drug to the specimen.

4. An ultrasonic Doppler diagnostic apparatus provided with a display unit, the apparatus sending ultrasonic waves to a specimen, receiving a reflection signal of the ultrasonic waves from the specimen to detect a Doppler signal and obtain information on flow velocities in the specimen to acquire a flow velocity waveform, and displaying the flow velocity waveform on the display unit, the apparatus comprising:

an extraction unit which extracts a first flow velocity value at a first time point within a first heartbeat from the flow velocity waveform, and a second flow velocity value at a second time point within a second heartbeat from the flow velocity waveform;

a control unit which controls the display unit to draw first and second temporal changes of the first and second flow velocity values that were extracted from the flow velocity waveform within the first and second heartbeats, respectively; and a trimming and adjustment unit configured to adjust and trim the first temporal change and the second temporal change of the first and second flow velocity values, respectively, to a same velocity range.

5. The ultrasonic Doppler diagnostic apparatus according to claim 4, further comprising:

a notification unit which notifies an operator that the flow velocity waveform displayed by the display unit is equal to a peak flow velocity when an acquired value of the flow velocity waveform is equal to the peak flow velocity.

6. The ultrasonic Doppler diagnostic apparatus according to claim 4, wherein the control unit uses a biological signal as a trigger signal to cause the display unit to draw a locus of the temporal changes for at least one heartbeat.

7. The ultrasonic Doppler diagnostic apparatus according to claim 4, wherein the control unit reads a specified part of the flow velocity waveform.

8. The ultrasonic Doppler diagnostic apparatus according to claim 4, wherein the control unit further controls the display unit to simultaneously display the flow velocity waveform and the temporal changes of the first and the second flow velocity values extracted by the extraction unit.

9. The ultrasonic Doppler diagnostic apparatus according to claim 8, wherein
the display unit further displays a message indicating that the flow velocity waveform has reached a peak flow velocity value.

10. A method of controlling an ultrasonic Doppler diagnostic apparatus, the method comprising the steps of:
sending ultrasonic waves to a specimen;
receiving a reflection signal of the ultrasonic waves from the specimen to detect a Doppler signal and obtain information on flow velocities in the specimen;
trimming a first flow velocity information acquired at a first time period of different time points and a second flow velocity information acquired at a second time period of different time points from the information on the flow velocities to a same velocity range;
first adjusting the first flow velocity information acquired at the first time period of different time points to the same velocity range;
second adjusting the second flow velocity information acquired at the second time period of different time points to the same velocity range; and
controlling to simultaneously display the first and the second flow velocity information of the first and the second time period adjusted and trimmed to the same velocity range.

11. A method of controlling an ultrasonic Doppler diagnostic apparatus, the method comprising the steps of:
sending ultrasonic waves to a specimen;
receiving a reflection signal of the ultrasonic waves from the specimen to detect a Doppler signal and obtain information on flow velocities in the specimen to acquire a flow velocity waveform;
displaying the flow velocity waveform;
extracting a first flow velocity value at a first time point within a first heartbeat from the flow velocity waveform, and a second flow velocity value at a second time point within a second heartbeat from the flow velocity waveform;
controlling to draw temporal changes of the first and the second flow velocity values that were extracted within the first and the second heartbeats, respectively; and
trimming and adjusting the temporal changes of the first and second flow velocity values, respectively, to a same velocity range.

* * * * *